(12) United States Patent
Patton (10) Patent No.: US 11,540,943 B2
(45) Date of Patent: Jan. 3, 2023

(54) SYSTEMS AND METHODS FOR COMBINED FEMTO-PHACO CATARACT SURGERY

(71) Applicant: Douglas Patton, Irvine, CA (US)

(72) Inventor: Douglas Patton, Irvine, CA (US)

(73) Assignee: Lensar, Inc., Orlando, FL (US)

( * ) Notice: Subject to any disclaimer, the term of this patent is extended or adjusted under 35 U.S.C. 154(b) by 137 days.

(21) Appl. No.: 16/219,700

(22) Filed: Dec. 13, 2018

(65) Prior Publication Data

US 2019/0117460 A1 Apr. 25, 2019

Related U.S. Application Data

(63) Continuation of application No. 14/666,908, filed on Mar. 24, 2015, now Pat. No. 10,285,858, which is a continuation of application No. 13/648,196, filed on Oct. 9, 2012, now Pat. No. 8,986,290.

(60) Provisional application No. 61/543,930, filed on Oct. 6, 2011.

(51) Int. Cl.
*A61F 9/008* (2006.01)
*A61F 9/007* (2006.01)

(52) U.S. Cl.
CPC ...... *A61F 9/00802* (2013.01); *A61F 9/00745* (2013.01); *A61F 9/00825* (2013.01); *A61F 2009/0087* (2013.01); *A61F 2009/00872* (2013.01); *A61F 2009/00887* (2013.01)

(58) Field of Classification Search
CPC .. A61F 9/008; A61F 9/00802; A61F 9/00804; A61F 9/00825; A61F 2009/00861; A61F 2009/0087; A61F 2009/00885; A61F 2009/00887; A61F 2009/00889

USPC ............... 606/4, 6, 13–15, 170; 604/19, 22
See application file for complete search history.

(56) References Cited

U.S. PATENT DOCUMENTS

| | | | |
|---|---|---|---|
| 4,729,373 A | 3/1988 | Peyman | |
| 4,825,865 A | 5/1989 | Zelman | |
| 4,946,452 A | 8/1990 | Py | |
| 4,963,142 A | 10/1990 | Loertscher | |

(Continued)

FOREIGN PATENT DOCUMENTS

| | | |
|---|---|---|
| EP | 2057973 | 5/2009 |
| JP | 2015 02964 | 2/2015 |

(Continued)

OTHER PUBLICATIONS

Dalton, M., "Cataract Surgery—Femto lasers in cataract surgery: The Best of Opthalmology", Eye World New Magazine, http://eyeworld.org/article.php?sid=5413, Apr. 2010.

(Continued)

*Primary Examiner* — Ahmed M Farah
(74) *Attorney, Agent, or Firm* — Glen P. Belvis; Belvis Law, LLC.

(57) ABSTRACT

Devices to perform femtolaser ablation and phacoemulsification are physically and/or operationally combined. In some embodiments the femtolaser ablation and phacoemulsification are housed together, and in other embodiments they are housed separately, but operated through a common display screen. At least some software can be shared by the femtolaser ablation and phacoemulsification functionalities. A non-transitory computer-readable memory can provide data that can be used to operate each of at least one femtolaser ablation functionality and at least one phacoemulsification functionality.

3 Claims, 9 Drawing Sheets

(56) References Cited

U.S. PATENT DOCUMENTS

| | | | |
|---|---|---|---|
| 5,057,098 A | 10/1991 | Zelman | |
| 5,098,426 A | 3/1992 | Sklar | |
| 5,139,504 A | 8/1992 | Zelman | |
| 5,222,952 A | 6/1993 | Loertscher | |
| 5,423,801 A | 6/1995 | Marshall | |
| 5,455,766 A | 10/1995 | Scheller et al. | |
| 5,478,338 A | 12/1995 | Reynard | |
| 5,548,352 A | 8/1996 | Dewey | |
| 5,591,160 A | 1/1997 | Reynard | |
| 5,651,783 A | 7/1997 | Reynard | |
| 5,695,461 A | 12/1997 | Schaible | |
| 5,722,970 A | 3/1998 | Colvard et al. | |
| 5,741,244 A | 4/1998 | Klaas | |
| 6,045,527 A | 4/2000 | Appelbaum | |
| 6,328,732 B1 | 12/2001 | Donitzky et al. | |
| 6,391,020 B1* | 5/2002 | Kurtz | A61B 18/22 606/2.5 |
| 6,454,763 B1 | 9/2002 | Motter et al. | |
| 6,544,254 B1* | 4/2003 | Bath | A61F 9/008 606/6 |
| 6,623,477 B1* | 9/2003 | Elbrecht | A61F 9/00802 606/4 |
| 6,726,680 B1* | 4/2004 | Knopp | A61B 3/13 606/12 |
| 6,733,491 B2 | 5/2004 | Kadziauskas | |
| 6,962,583 B2 | 11/2005 | Kadziauskas | |
| 7,137,980 B2 | 11/2006 | Buysse et al. | |
| 7,182,759 B2 | 2/2007 | Kadziauskas | |
| 8,394,084 B2 | 3/2013 | Palankar et al. | |
| 8,403,921 B2 | 3/2013 | Palankar et al. | |
| 8,986,290 B2 | 3/2015 | Patton | |
| 9,050,171 B2 | 6/2015 | Foster | |
| 9,095,415 B2 | 8/2015 | Blumenkranz et al. | |
| 9,107,732 B2 | 8/2015 | Blumenkranz et al. | |
| 9,259,354 B2 | 2/2016 | Horvath | |
| 9,492,318 B2 | 11/2016 | Rockley et al. | |
| 10,709,610 B2 | 7/2020 | Morley et al. | |
| 2002/0013574 A1 | 1/2002 | Elbrecht et al. | |
| 2003/0050629 A1 | 3/2003 | Kadziauskas | |
| 2003/0073984 A1 | 4/2003 | Maeda | |
| 2004/0034340 A1 | 2/2004 | Biscup | |
| 2007/0027470 A1 | 2/2007 | Dodick | |
| 2007/0173794 A1 | 7/2007 | Frey et al. | |
| 2007/0237620 A1 | 10/2007 | Muhlhoff | |
| 2008/0004608 A1 | 1/2008 | Dacquay | |
| 2008/0071254 A1 | 3/2008 | Lummis | |
| 2008/0281303 A1 | 11/2008 | Culbertson et al. | |
| 2009/0049522 A1* | 2/2009 | Claus | G16Z 99/00 726/4 |
| 2009/0088734 A1 | 4/2009 | Mordaunt | |
| 2009/0137991 A1 | 5/2009 | Kurtz | |
| 2009/0247999 A1 | 10/2009 | Tuan et al. | |
| 2010/0076453 A1* | 3/2010 | Morris | G16H 40/40 606/130 |
| 2010/0137983 A1 | 6/2010 | Culbertson et al. | |
| 2010/0156646 A1 | 6/2010 | Cull et al. | |
| 2010/0191226 A1* | 7/2010 | Blumenkranz | A61F 9/00836 606/4 |
| 2010/0191230 A1 | 7/2010 | Dick et al. | |
| 2010/0324542 A1* | 12/2010 | Kurtz | A61F 9/00825 606/6 |
| 2011/0022035 A1 | 1/2011 | Porter | |
| 2011/0288470 A1 | 11/2011 | Boukhny | |
| 2013/0023864 A1* | 1/2013 | Blumenkranz | A61B 90/361 606/6 |
| 2013/0090636 A1 | 4/2013 | Patton | |
| 2013/0150836 A1* | 6/2013 | Bor | A61F 9/00831 606/4 |
| 2014/0052113 A1 | 2/2014 | Kuehnert | |
| 2014/0104576 A1 | 4/2014 | Bor et al. | |
| 2014/0107634 A1 | 4/2014 | Volgar | |
| 2014/0364870 A1 | 12/2014 | Alvarez et al. | |
| 2015/0190281 A1 | 6/2015 | Patton | |
| 2016/0045367 A1 | 2/2016 | Horvath | |
| 2016/0089269 A1 | 3/2016 | Horvath | |
| 2016/0235586 A1* | 8/2016 | Fu | A61F 9/00825 |
| 2017/0000645 A1 | 1/2017 | Summers et al. | |
| 2017/0000647 A1 | 1/2017 | Schuele et al. | |
| 2017/0056245 A1 | 3/2017 | Rockley et al. | |
| 2017/0119249 A1 | 5/2017 | Gunn | |
| 2017/0119578 A1 | 5/2017 | Rockley et al. | |
| 2017/0340483 A1 | 5/2017 | Rill et al. | |
| 2017/0290703 A1 | 10/2017 | Teuma et al. | |
| 2018/0028355 A1 | 2/2018 | Rockley et al. | |
| 2018/0085256 A1 | 3/2018 | Gray et al. | |
| 2018/0161051 A1 | 6/2018 | Humayun | |
| 2018/0168859 A1 | 6/2018 | Bischoff et al. | |
| 2018/0185043 A1 | 7/2018 | Humayun | |
| 2018/0206717 A1 | 7/2018 | Ramesh Kumar et al. | |
| 2018/0250090 A1 | 9/2018 | Patton | |
| 2019/0083308 A1 | 3/2019 | Rathjen | |
| 2019/0096933 A1 | 3/2019 | Kido et al. | |
| 2019/0365567 A1 | 12/2019 | Balkenbush et al. | |
| 2020/0345431 A1* | 11/2020 | Patton | G09B 23/28 |
| 2021/0259880 A1 | 8/2021 | Newton et al. | |
| 2021/0259881 A1 | 8/2021 | Gray et al. | |
| 2021/0298955 A1 | 9/2021 | McWhirter et al. | |
| 2021/0378864 A1 | 12/2021 | Teuma et al. | |

FOREIGN PATENT DOCUMENTS

| | | |
|---|---|---|
| WO | WO1992017138 | 10/1992 |
| WO | WO1997022304 | 6/1997 |
| WO | WO1998012973 | 4/1998 |
| WO | WO 1999065405 | 12/1999 |
| WO | 2006/073400 A1 | 7/2006 |
| WO | WO2006074469 | 7/2006 |
| WO | 2009/023809 A1 | 2/2009 |
| WO | WO2009039315 | 3/2009 |
| WO | WO2009061758 | 5/2009 |
| WO | 2011/147570 A1 | 12/2011 |
| WO | WO2012047492 | 4/2012 |
| WO | WO 2013057098 | 4/2013 |
| WO | WO2013126653 | 8/2013 |
| WO | WO2014201165 | 12/2014 |

OTHER PUBLICATIONS

"Femto-Cataract", Technolas Perfect Vision, http://www.technolaspv.com/dasal/index.php?cid=100858, screen capture Jan. 10, 2013.

"Phacoemulsification", Wikipedia, The Free Encyclopedia, http://en.wikipedia.org/wiki/Phacoemulsification, screen capture Jan. 10, 2013.

Jul. 7, 2021, WIPO, 2021/0259880—Opinion and search report.
Apr. 6, 2021, WIPO, 2021/0259881—Opinion and search report.
May 25, 2021, WIPO, 2021/0298955—Opinion and search report.
Jun. 25, 2021, WIPO, 2021/0378864—Opinion and search report.

* cited by examiner

SYSTEMS AND METHODS FOR COMBINED FEMTO-PHACO CATARACT SURGERY

This application claims priority to U.S. Ser. No. 14/666,908, filed Mar. 24, 2015, which claims priority to U.S. Ser. No. 13/648,196, filed Oct. 9, 2012, which claims priority to U.S. Provisional Application No. 61/543,930, filed Oct. 6, 2011, each of which is incorporated herein by reference in its entirety.

FIELD OF THE INVENTION

The field of the invention is cataract surgery.

BACKGROUND

Modern cataract surgery is commonly performed using phacoemulsification, which is colloquially known as "phaco". In that process the internal lens of an eye is emulsified with an ultrasonic handpiece, and the detritus is aspirated from the eye. Aspirated fluids are replaced with irrigation of balanced salt solution. As with other cataract extraction procedures, an intraocular lens implant (IOL), is placed into the remaining lens capsule. See http://en.wikipedia.org/wiki/Phacoemulsification.

The referenced Wikipedia article, as well as all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

The phaco probe is an ultrasonic handpiece with a titanium or steel needle. The tip of the needle vibrates at ultrasonic frequency to sculpt and emulsify the cataract, while the pump aspirates particles through the tip. In some techniques, a second fine steel instrument called a "chopper" is used from a side port to help with chopping the nucleus into smaller pieces. The cataract is usually broken into two or four pieces and each piece is emulsified and aspirated out with suction. The nucleus emulsification makes it easier to aspirate the particles. After removing all hard central lens nucleus with phacoemulsification, the softer outer lens cortex is removed with suction only.

Figure 1:
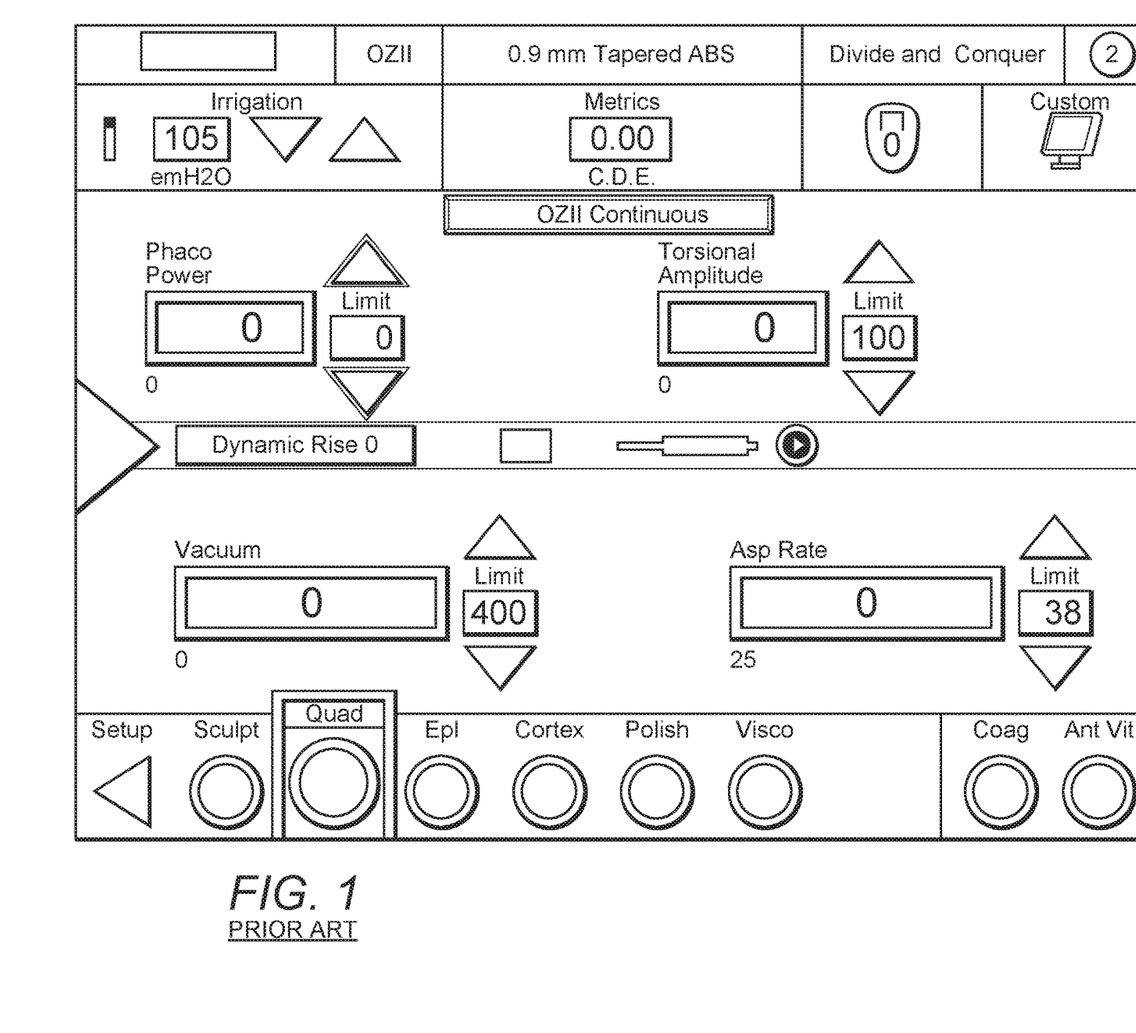
FIG. 1 is a screen shot of a prior art graphical user interface for a phacoemulsification device.
Figure 2:
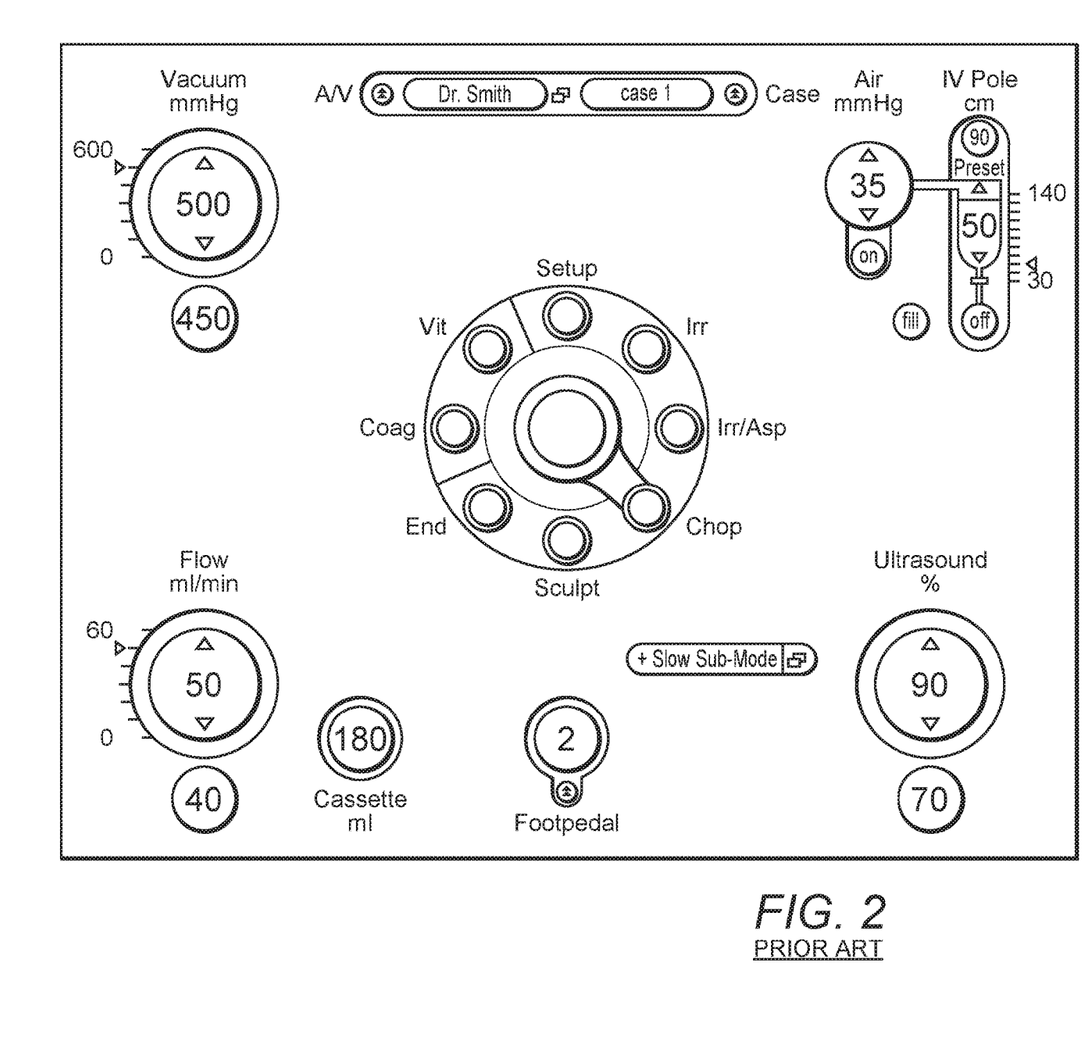
FIG. 2 is a screen shot of an alternative prior art graphical user interface for a phacoemulsification device.
Figure 3:
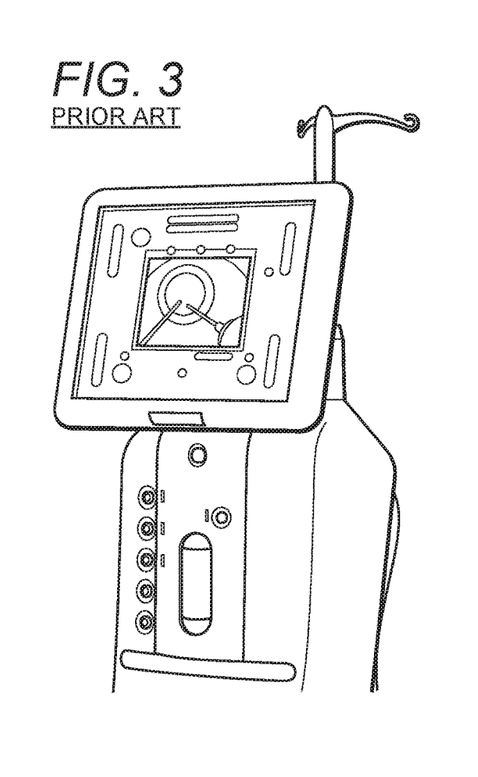
FIG. 3 is a prior art representation of the phacoemulsification device of FIGS. 1 and 2.
Figure 4:
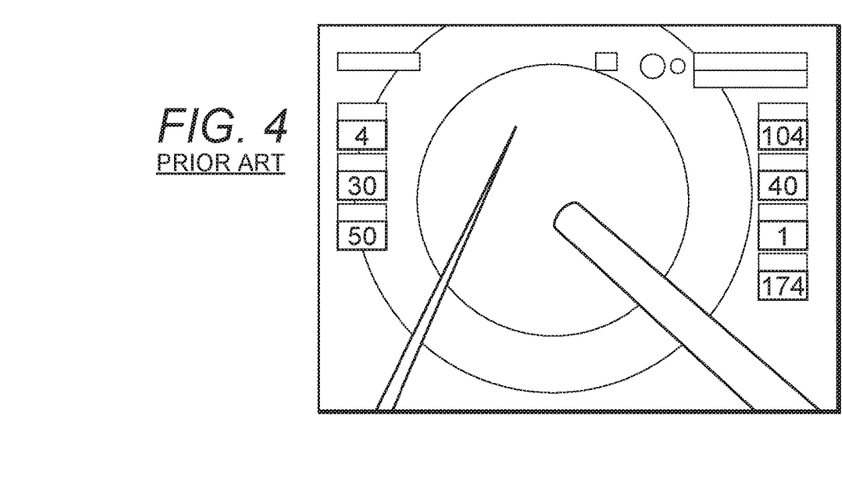
FIG. 4 is a prior art representation of a display of the phacoemulsification device of FIGS. 1 and 2, showing an eye during phacoemulsification.
Figure 5:
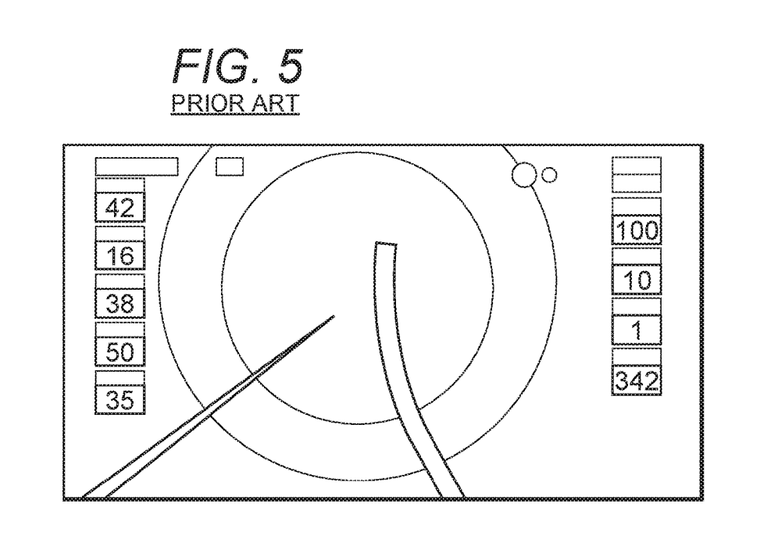
FIG. 5 is a prior art representation of a display of the phacoemulsification device of FIGS. 1 and 2, showing an eye during aspiration.
Figure 6:
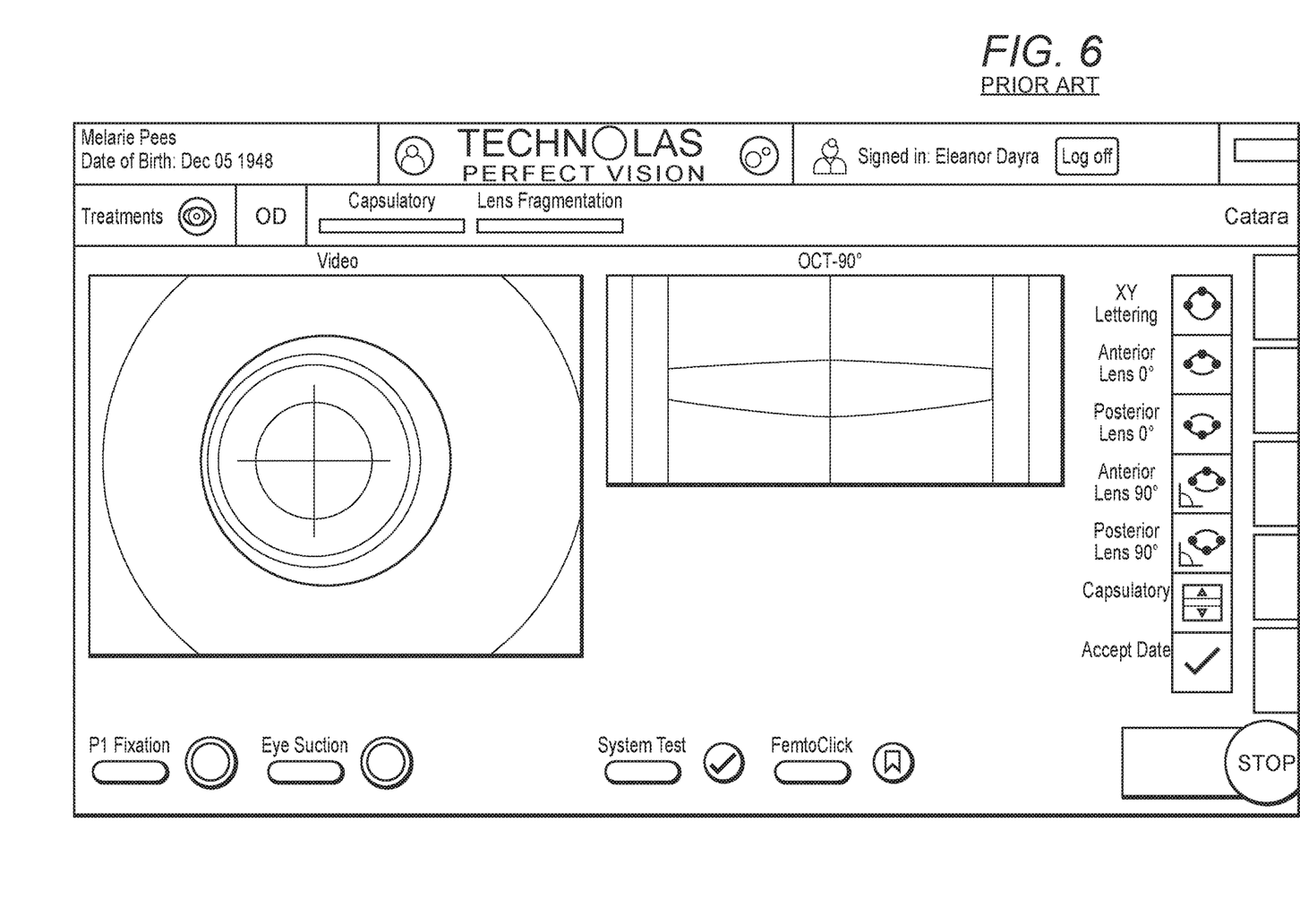
FIG. 6 is a prior art screen shot of a prior art graphical user interface for a femtolaser ablation device.
Figure 7:
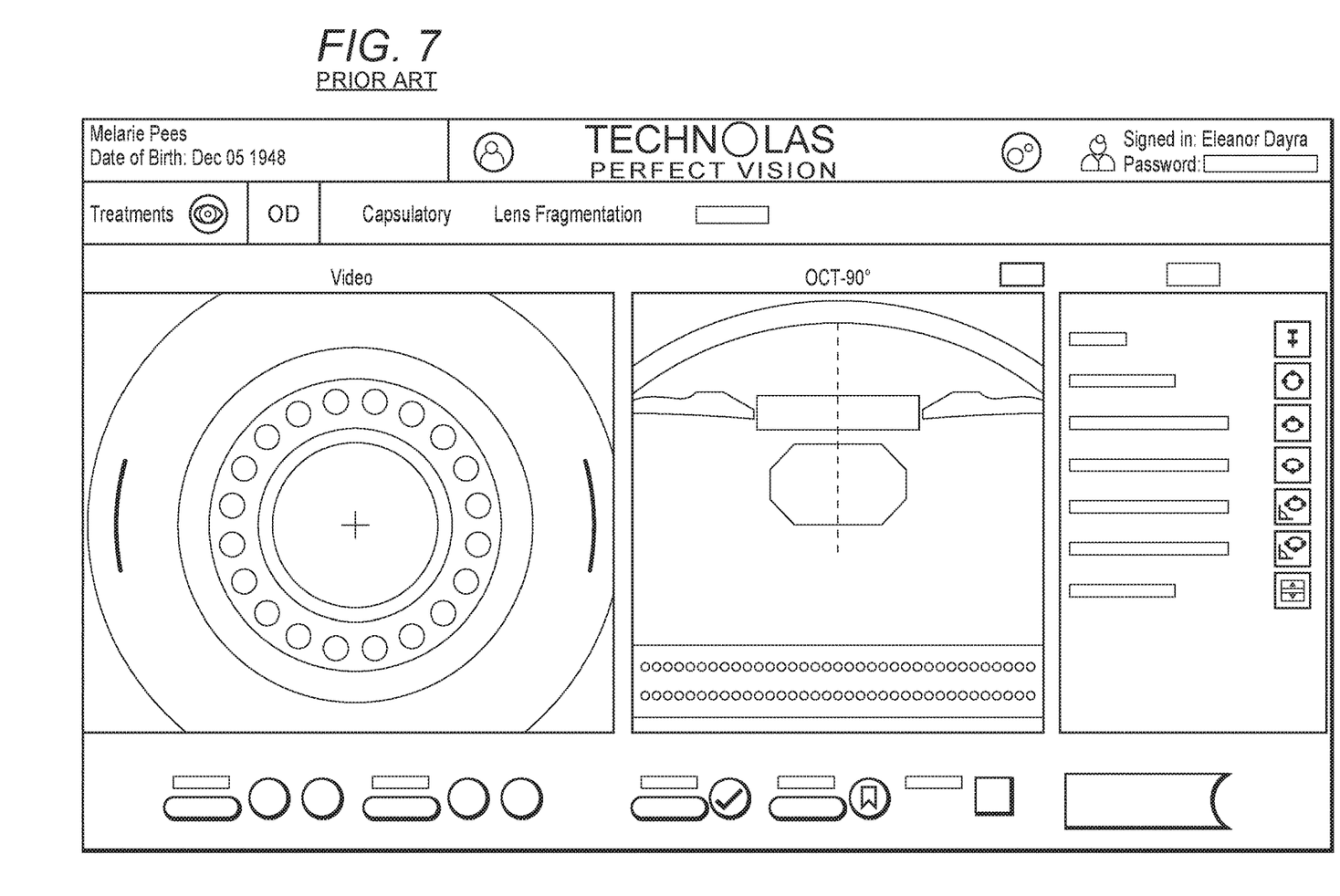
FIG. 7 is a screen shot of another prior art graphical user interface of the femtolaser ablation device of FIG. 3.
Figure 8:
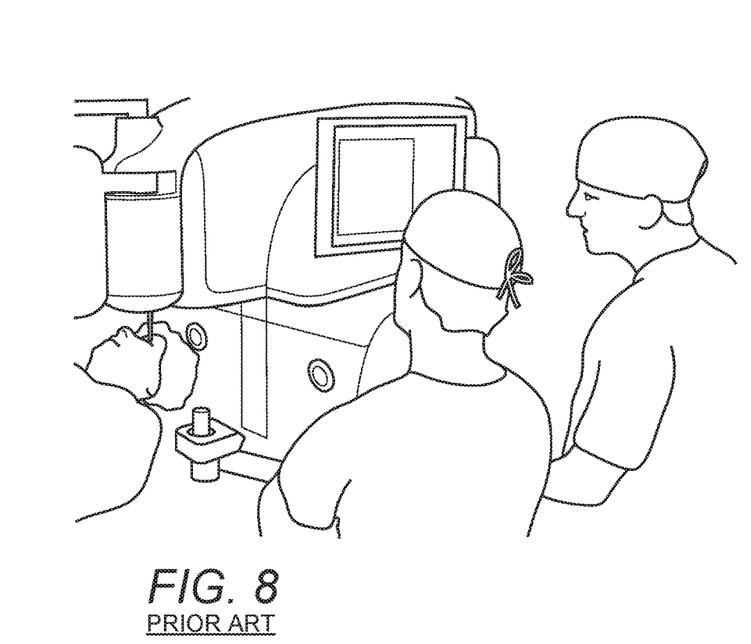
FIG. 8 is a prior art representation medical personnel using the femtolaser ablation device of FIGS. 6 and 7.
Figure 9:
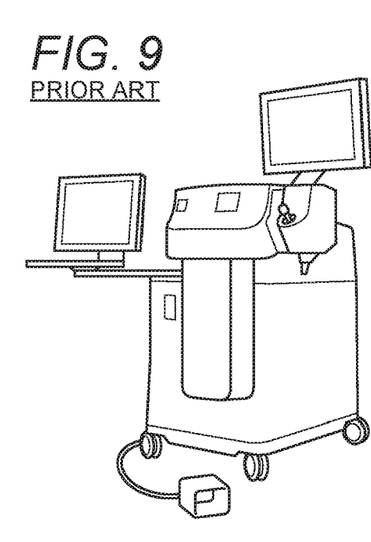
FIG. 9 is a prior art representation medical personnel using the femtolaser ablation device of FIGS. 6 and 7.
Figure 10:
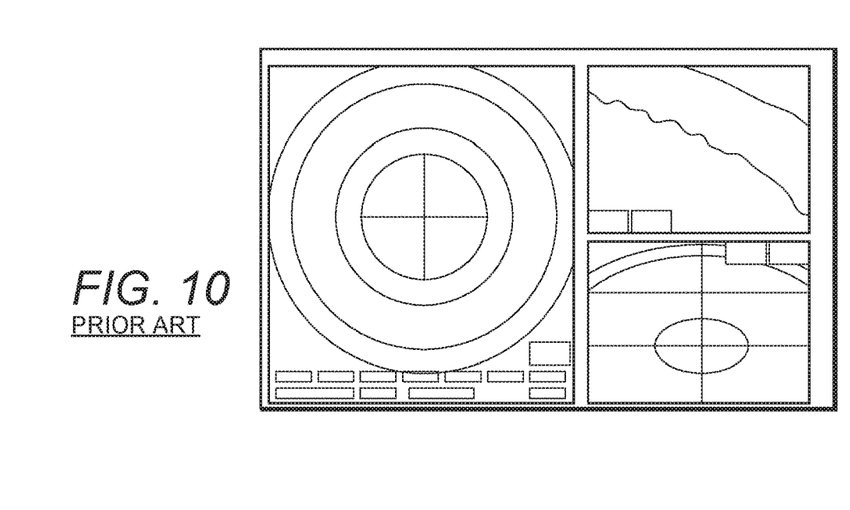
FIG. 10 is another prior art representation of a femtolaser ablation device.

Phacoemulsification surgery involves the use of a machine with microprocessor-controlled fluid dynamics. Emulsification power applied through the probe, vacuum strength of the aspirator, and other operating parameters of the phaco device are controlled through software. Examples of graphic user interfaces of popular phacoemulsification software are depicted in prior art FIGS. 1 and 2.

Before phacoemulsification can be performed, one or more incisions are typically made in the eye to allow the introduction of surgical instruments. The surgeon then removes the anterior face of the capsule that contains the lens inside the eye. During that part of the procedure, difficulties sometimes arise during the incision portion of the procedure, potentially causing damage to the eye.

It is known to use femtosecond laser pulses to make incisions into the eye, and recently devices are available for remediating cataracts using femtolaser ablation. One device currently in the marketplace for accomplishing that is Technolas Perfect Vision's™ VICTUS™ Femtosecond Laser Platform. See http://www.technolaspv.com/dasat/index.php?cid=100858. Femtolaser ablation of cataracts can remove even fairly large cataracts quite quickly, but (1) some portions of cataract can remain, requiring phacoemulsification, and (2) detritus must still be removed using irrigation and aspiration.

Currently, cataract remediation using femtolaser ablation followed by phacoemulsification is performed by two entirely separate machines, requiring translocation and re-setup of the patient. This increases the time required for the procedure, and can cause undue stress on the patient.

Thus, there is a need to combine femtolaser ablation and phacoemulsification either in the same device, or at least in separate devices that are operated using a combined software platform.

SUMMARY OF THE INVENTION

The inventive subject matter provides apparatus, systems and methods in which devices to perform femtolaser ablation and phacoemulsification are physically and/or operationally combined.

In one aspect, at least one subsystem of the femtolaser ablation functionality is housed in a common housing with at least one subsystem of the phacoemulsification functionality.

In another aspect, a display screen displays both a first graphical user interface for the femtolaser ablation functionality and a second graphical user interface for the phacoemulsification functionality.

In another aspect, software includes instructions disposed on a non-transitory computer-readable medium that are common to operation of both the femtolaser ablation functionality and the phacoemulsification functionality.

In another aspect a non-transitory computer-readable memory provides data that can be used to operate each of the femtolaser ablation functionality and the phacoemulsification functionality.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

As seen in FIGS. 11-15, it is contemplated that a single GUI and/or software can combine control of ophthalmic phacoemulsification and femtolaser functionalities for cataract removal. These can be combined in many diverse ways for surgical use on at least one of a computer touch screen, a set of dedicated buttons, a foot pedal, and a voice interface.

Figure 11:
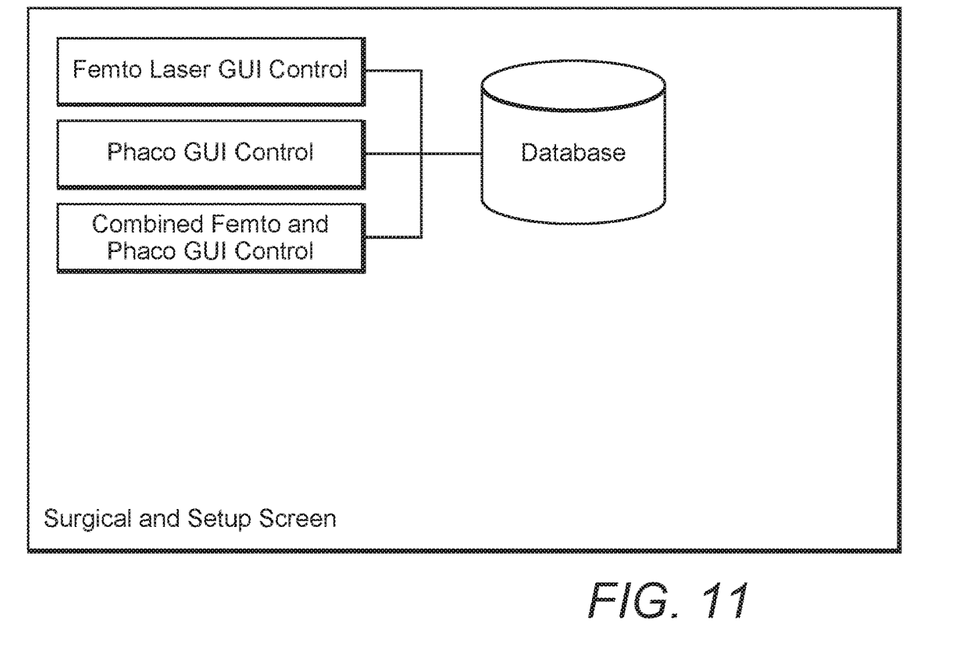
FIG. 11 is a schematic of a graphical user interface of software configured to control both a femtolaser ablation device and a phacoemulsification device.

FIG. 11 is a schematic of a graphical user interface of software configured to control both a femtolaser ablation device and a phacoemulsification device. The platform can be local to one or more of the devices, and can alternatively or additionally be at least partially disposed on one or more distal servers (e.g., cloud, PaaS, IaaS, SaaS, etc.). Each of the devices shown in the figures should be interpreted as including electronics and software needed to operate the device, and the software should be interpreted as capable of reading and utilizing data from one or more databases.

Devices shown in the figures with connecting lines should be interpreted as being at least functionally coupled to one another, and in some embodiments physically coupled to one another. Thus, a display device shown with a connecting line to a femtolaser ablation device should be interpreted as being at least electronically coupled to one another. As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. The terms "coupled to" and "coupled with" are also use euphemistically to mean "communicatively coupled with" in a networking sense where at least two networked elements are able to communicate with each other over a network possibly via one or more intermediary devices.

It should be noted that any language directed to a computer or software platform should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

Figure 12:
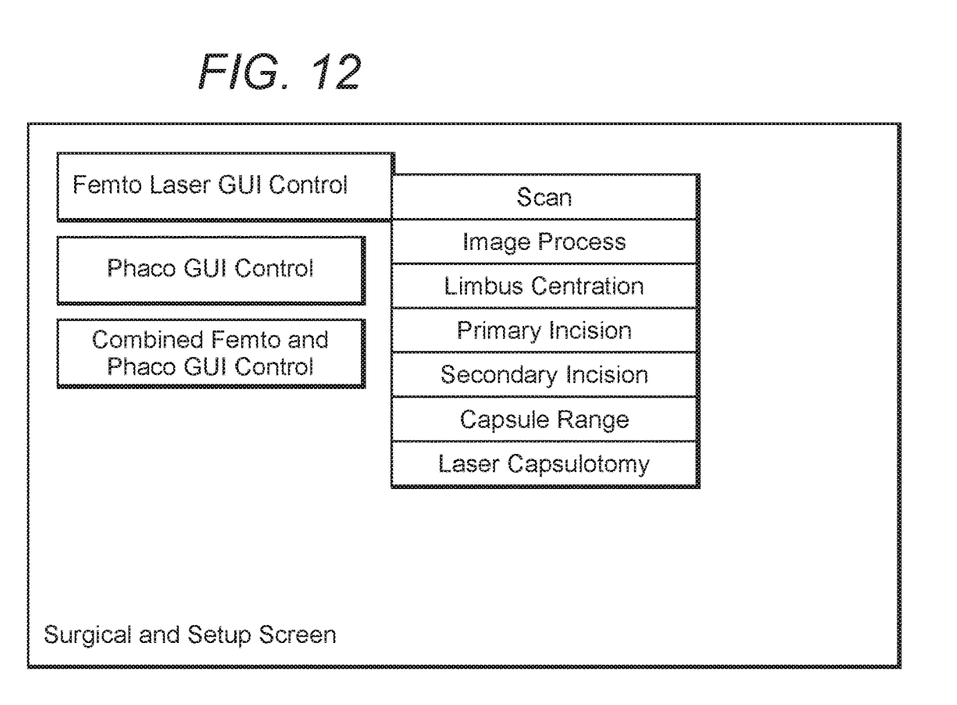
FIG. 12 is a schematic of the graphical user interface of FIG. 11, showing a menu of procedures that can be selected for the femtolaser ablation device.

FIG. 12 is a schematic of the graphical user interface of FIG. 11, showing a menu of procedures that can be selected for the femtolaser ablation device. These are exemplary procedures only, and contemplated femtolaser GUI interfaces may list other or additional procedures. One should also appreciate that each of FIGS. 12-15 are merely schematics, and commercial embodiments of the interfaces would be much more detailed and user friendly, such as along the lines of that shown in FIG. 1 or 2.

Figure 13:
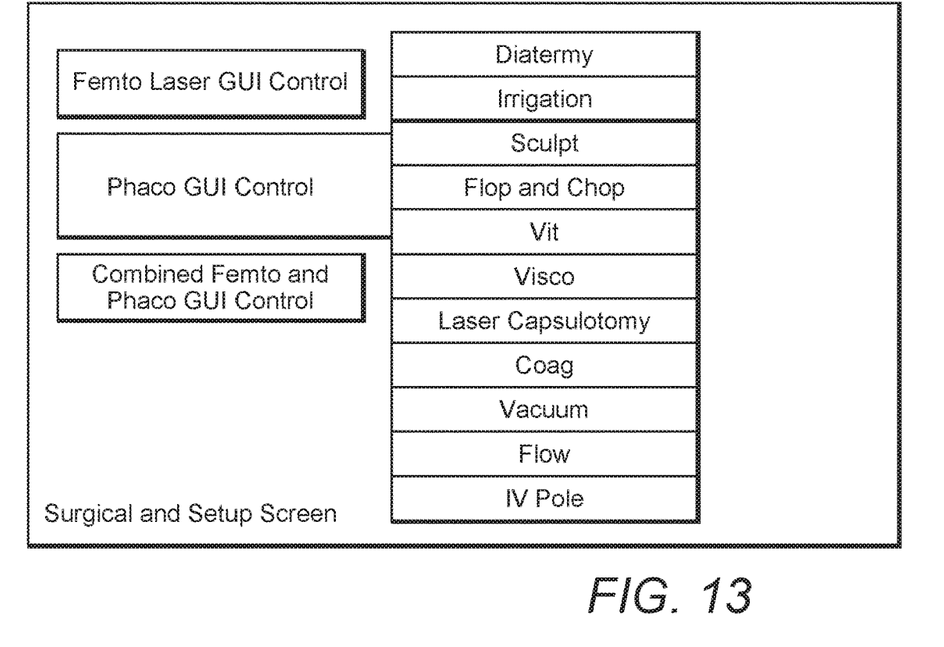
FIG. 13 is a schematic of the graphical user interface of FIG. 11, showing a menu of procedures that can be selected for the phacoemulsification device.

FIG. 13 is a schematic of the graphical user interface of FIG. 11, showing a menu of procedures that can be selected for the phacoemulsification device.

Figure 14:
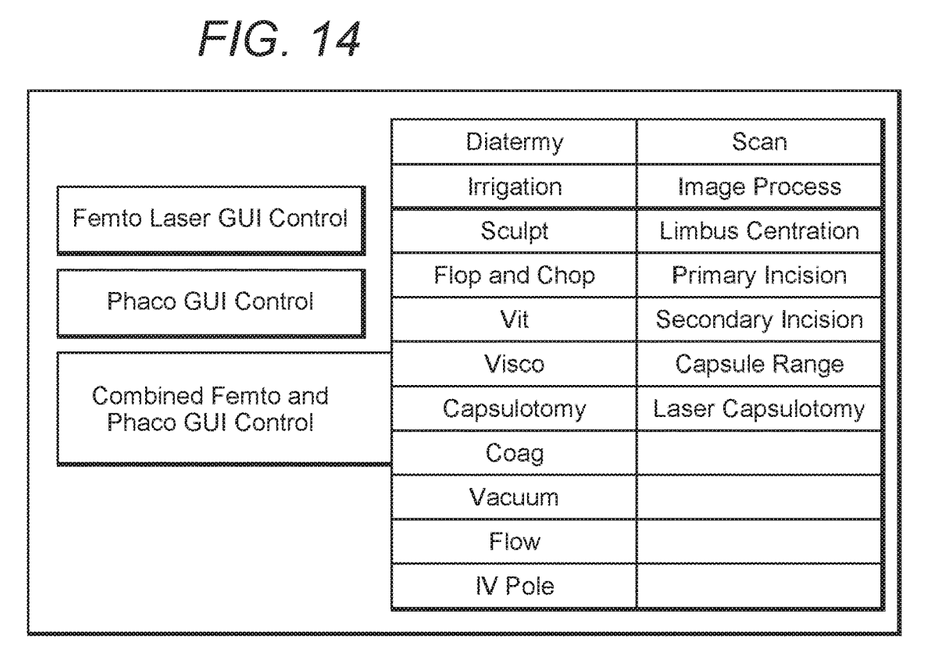
FIG. 14 is a schematic of the graphical user interface of FIG. 11, concurrently showing menus of procedures that can be selected for the femtolaser ablation device and the phacoemulsification device.

FIG. 14 is a schematic of the graphical user interface of FIG. 11, concurrently showing menus of procedures that can be selected for separate femtolaser ablation and phacoemulsification devices.

Figure 15:
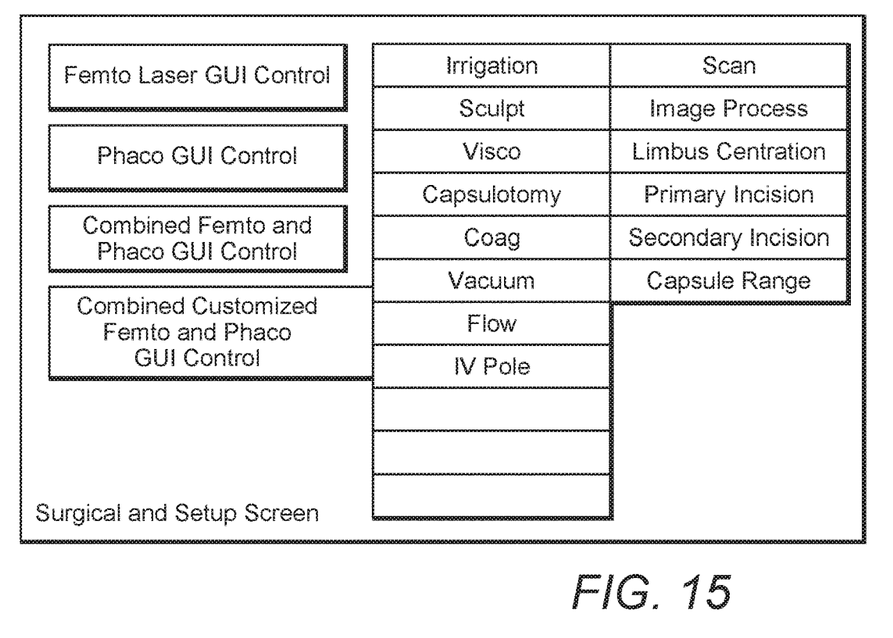
FIG. 15 is a schematic of a graphical user interface concurrently showing menus of procedures that can be selected for a device that combines femtolaser ablation functionality and phacoemulsification functionality.

FIG. 15 is a schematic of a graphical user interface concurrently showing menus of procedures that can be selected for a device that combines femtolaser ablation functionality and phacoemulsification functionality. This interface differs from that shown in FIG. 14 because the listing of functionalities is customized in some manner, for example by including custom functionalities not programmed into off-the-shelf devices, and/or by hiding functionalities that might otherwise be available. Such customization of main menu and/or submenu procedures for phaco and femto could be arranged by the manufacturer and/or or surgeon in an order that is thought to best fit the process of cataract removal and soft lens insertion for a particular practitioner or office.

Figure 16:
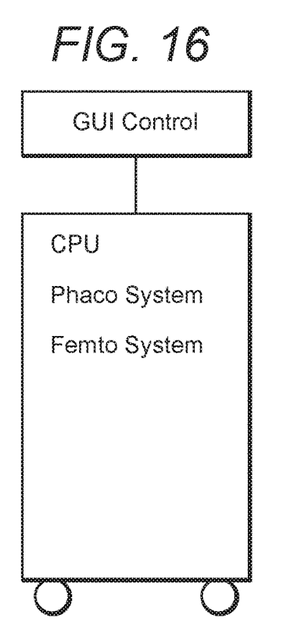
FIG. 16 is a schematic of a device that combines femtolaser ablation functionality and phacoemulsification functionality, using a common GUI control platform.
Figure 17:
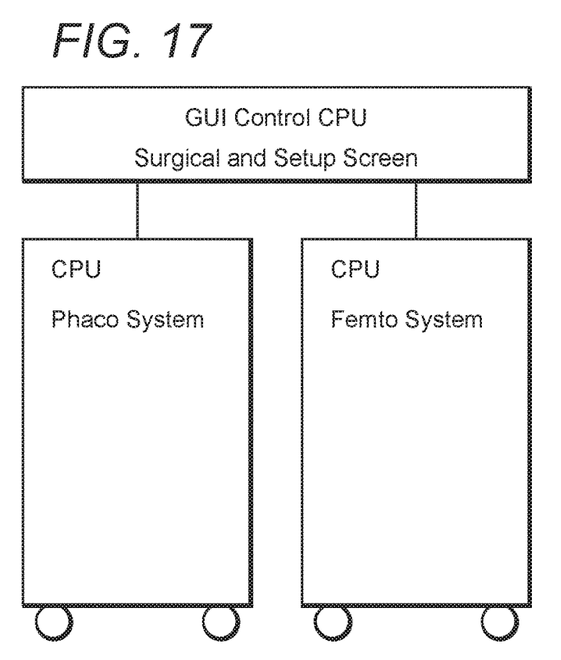
FIG. 17 is a schematic of a device that utilizes a common GUI control platform to control physically separate femtolaser ablation and phacoemulsification devices.

FIG. 16 is a schematic of a device that combines femtolaser ablation functionality and phacoemulsification functionality, using a common GUI control platform. FIG. 17 is a schematic of a device that utilizes a common GUI control platform to control physically separate femtolaser ablation and phacoemulsification devices. Each of the interfaces of FIGS. 12-15 could be used with each of the embodiments shown in FIGS. 16 and 17.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of operating a combined device having a femto second laser and a phacoemulsification device, for removing a cataract from an eye, comprising:
    providing submenus for both a phacoemulsification procedure and a femto laser procedure on a single GUI; wherein the GUI is associated with a combined device comprising a femto second laser and a phacoemulsification device; and,
    using at least one of a computer touchscreen, dedicated buttons, a foot pedal, and voice interaction to combine in multiple different ways, the phacoemulsification and femto laser procedures accessed by the submenus;
    wherein the phacoemulsification procedures include diathermy, irrigation, sculpt, flop and chop, vit, and visco.

2. A method of operating a combined device having a femto second laser and a phacoemulsification device, for removing a cataract from an eye, comprising:
    providing submenus for both a phacoemulsification procedure and a femto laser procedure on a single GUI; wherein the GUI is associated with a combined device comprising a femto second laser and a phacoemulsification device; and,
    using at least one of a computer touchscreen, dedicated buttons, a foot pedal, and voice interaction to combine in multiple different ways, the phacoemulsification and femto laser procedures accessed by the submenus;
    wherein the femto laser procedures include scan, image process, limbus centration, primary incision, secondary incision, capsule range, and laser capsulotomy.

3. A method of operating a combined device having a femto second laser and a phacoemulsification device, for removing a cataract from an eye, comprising:
    providing submenus for both a phacoemulsification procedure and a femto laser procedure on a single GUI; wherein the GUI is associated with a combined device comprising a femto second laser and a phacoemulsification device; and,
    using at least one of a computer touchscreen, dedicated buttons, a foot pedal, and voice interaction to combine in multiple different ways, the phacoemulsification and femto laser procedures accessed by the submenus;
    further including a database having data that describes a main menu and the submenu for both the phacoemulsification and the femto laser procedures.

* * * * *